US006985558B1

(12) United States Patent
Russell

(10) Patent No.: US 6,985,558 B1
(45) Date of Patent: Jan. 10, 2006

(54) INTERMEDIATE DENSITY MARKER AND A METHOD USING SUCH A MARKER FOR RADIOGRAPHIC EXAMINATION

(75) Inventor: Donald G. Russell, Kensington, CT (US)

(73) Assignee: Beekley Corporation, Bristol, CT (US)

( * ) Notice: Subject to any disclaimer, the term of this patent is extended or adjusted under 35 U.S.C. 154(b) by 1178 days.

(21) Appl. No.: 09/372,835

(22) Filed: Aug. 12, 1999

Related U.S. Application Data

(63) Continuation of application No. 08/934,121, filed on Sep. 19, 1997, now Pat. No. 6,041,094, which is a continuation of application No. 08/372,658, filed on Jan. 13, 1995, now abandoned, which is a continuation-in-part of application No. 08/059,201, filed on May 7, 1993, now Pat. No. 5,383,233.

(51) Int. Cl.
*H05G 1/28* (2006.01)
(52) U.S. Cl. ..................................................... 378/162
(58) Field of Classification Search ................ 378/162, 378/165, 163
See application file for complete search history.

(56) References Cited

U.S. PATENT DOCUMENTS

| 3,952,194 A | 4/1976 | Bayonnet ..................... 378/163 |
| 4,506,676 A | 3/1985 | Duska ......................... 378/165 |
| 5,052,035 A | 9/1991 | Krupnick ..................... 378/163 |
| 5,193,106 A | 3/1993 | Desena ....................... 378/163 |
| 5,394,456 A | 2/1995 | Livingston .................. 378/162 |
| 5,469,847 A | 11/1995 | Zinreich et al. ............ 378/162 |

*Primary Examiner*—Craig E. Church
(74) *Attorney, Agent, or Firm*—McCarter & English, LLP

(57) ABSTRACT

The present invention provides a partially radiolucent, partially radiopaque marker and a method for using such a marker for radiographic examination. The marker and the disclosed method may be employed for the examination of tissue structures of various densities. The radiographic density and thickness of the marker are selected so that when the marker and an underlying tissue structure are exposed to xray radiation of a specified energy, the marker casts a legible shadow without obscuring anatomical detail present in the underlying tissue structure. The invention also provides a system of partially radiolucent, partially radiopaque markers for use in the method of radiographic examination taught by the invention.

42 Claims, 6 Drawing Sheets

FIG. 4A                    FIG. 4B

INTERMEDIATE DENSITY MARKER AND A METHOD USING SUCH A MARKER FOR RADIOGRAPHIC EXAMINATION

This application is a continuation of application Ser. No. 08/934,121, filed Sep. 19, 1997, now U.S. Pat. No. 6,041,094, which is a continuation of application Ser. No. 08/372,658, filed Jan. 13, 1995, now abandoned, which is a continuation-in-part of application No. 08/059,201, filed May 7, 1993, now U.S. Pat. No. 5,383,233.

BACKGROUND OF THE INVENTION

The present invention relates generally to the field of radiography and, more particularly, to a marker of intermediate density and a method of radiographic examination using such a marker. The invention further relates to a system of radiographic markers for use in such a method.

To convey pertinent information on radiographic film, radiologists and technicians frequently use markers which absorb xrays and cast a shadow when placed within the xray exposure field. Such markers are positioned either directly on a patient undergoing radiographic examination or on the cassette holding the radiographic film.

For example, right and left markers are routinely used to designate the anatomical orientation of the patient or to identify a particular extremity being examined. Markers are also used in trauma cases to localize the trauma site by placing the marker on the skin surface at the appropriate location prior to x-ray exposure. Further, markers are often placed on the surface of the examination table or the film cassette, within the exposure field but outside the image of the patient, to define the patient's physical orientation in relationship to the xray beam or the film, i.e., erect, prone, supine or decubitus.

In the past, radiographic markers have been constructed of materials having a high atomic number such as, for example, lead, mercury, steel or heavy metal salts. When exposed to xrays, markers having such high density completely attenuate the xray beam and cast a distinct shadow that is readily apparent on the xray film. The disadvantage here is that any tissue detail that falls within the shadow of the marker will be completely obscured. Metallic markers also create problems when employed in computerized tomography (CT) applications. CT scanners, which typically operate in the range of 60 to 80 KV, cannot tolerate the presence of metallic objects in the radiographic field. Such dense objects cause streaking which degrades the radiographic image. This problem is made more acute by the fact that the marker must have sufficient surface area to be imaged in at least one section radiographed by the scanner. A metallic marker having the required surface area would completely disrupt the scanning apparatus.

Accordingly, it has been the practice of those skilled in the art of general radiography to place such markers on the patient or the radiographic film outside the area of clinical concern. This practice encourages increasing the size of the xray field to ensure that the image of an important marker appears on the film. Unfortunately, one result of such a practice is that the patient's body is exposed to potentially harmful radiation beyond the specific site being examined. In cases where a radiographic examination is conducted and the image of a marker is not clearly visible within the exposure field, the exam is often repeated to either enlarge the exposure field or to reposition the marker. Again, the unfortunate result is that the patient is exposed to greater dosage of potentially harmful radiation.

To precisely locate a tissue area of particular concern on the radiographic film following exposure, there are circumstances where a marker is placed on a patient and purposely imaged while overlying anatomical structures. In such a case, it is the usual practice of those skilled in the art to use a small, metal, spherical marker measuring no more than about 1 to 2 mm in diameter. While the shadow from such a small marker is less likely to obscure important tissue detail, the shadow may be mistaken for a physiological calcification or an opaque foreign body. Further, because such a marker is necessarily of small size with a correspondingly small shadow, there is an inherent difficulty in discerning variations in the size and shape of the marker's image on the film. Thus, the information that can be conveyed by markers of this type is limited.

Finally, markers comprising lead, mercury and other toxic heavy metals cannot be deposited in landfills or incinerated and thus present a potential environmental hazard if improperly disposed of. This problem is exacerbated by the fact that during radiographic examination procedures markers are often contaminated by body fluids. While contaminated markers can be sterilized, to save time and expense they are, more typically, discarded after only a single use.

It is therefore an object of the invention to provide a radiographic marker which may be placed on a tissue structure and imaged without obscuring underlying anatomical detail.

It is a further object of the invention to provide such marker which is constructed from non-toxic material.

It is a still further object of the invention to provide markers of this type in various sizes and shapes to convey pertinent information on radiographic film.

It is another object of the invention to provide a marker for use in CT applications which may be placed on a tissue structure and imaged without obscuring underlying anatomical detail.

It is yet another object of the invention to provide a method of radiographic examination using such markers.

SUMMARY OF THE INVENTION

The present invention meets these and other objects by providing a partially radiolucent, partially radiopaque marker for the radiographic examination of underlying tissue structures. The marker has a radiographic density and thickness selected to permit the marker to both cast a radiographic shadow and transmit sufficient radiation to image anatomical detail present in the tissue structure when the marker and the tissue structure are exposed to an xray beam.

In a second aspect, the invention provides a method for radiographic examination which includes the steps of providing a source of xray radiation capable of generating an xray beam of sufficient energy to image a tissue structure exposed to the beam, and positioning the above-described intermediate density marker between the source of the xray radiation and the tissue structure. Once the marker has been properly positioned, the marker and the tissue structure are exposed to the xray beam to generate a radiographic image of the structure with the shadow of the marker superimposed thereon. Since the radiographic density and thickness of the marker have been carefully selected to meet the criteria set forth above, anatomical detail present in the tissue structure is clearly visible through the shadow cast by the marker.

In another aspect, the present invention provides a system of intermediate density markers for use in the radiographic examination of tissue structures representing a range of tissue densities. Tissues representing the range of densities for which the markers comprising the system may be used include, for example: breast tissue and other soft tissues having a density approximately equal to that of water; intermediate density tissues, such as the bones of the extremities; and very dense tissues such as the skull, spine and the tissues comprising the chest and other thick body parts.

Each of the markers comprising the system has a radiographic density and thickness which permit the marker, upon exposure of the marker and an underlying tissue structure to xray radiation of a specified energy, to both cast a radiographic shadow and transmit sufficient radiation to image anatomical detail present in the underlying tissue structure.

DETAILED DESCRIPTION OF THE INVENTION

Figure 1:
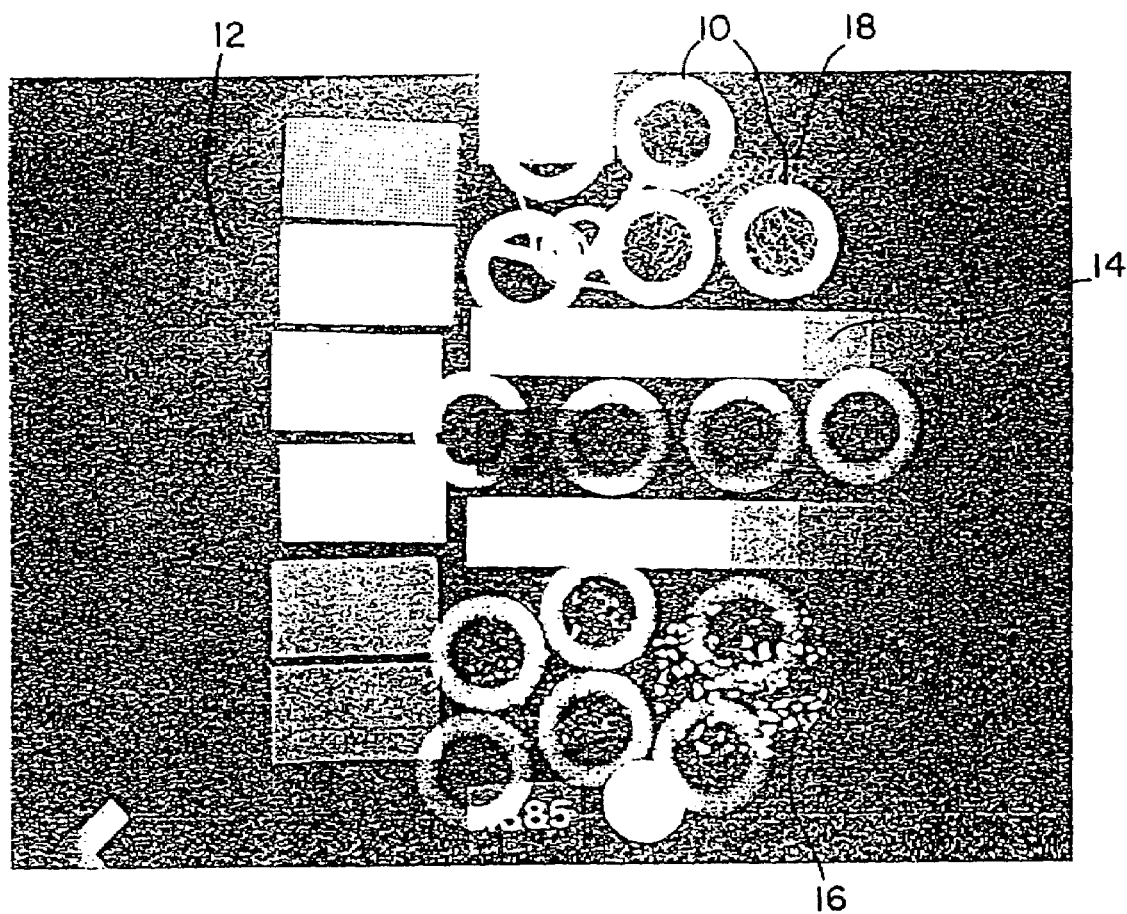
FIG. 1 is a radiograph of several rubber collars useful in practicing the method of the present invention imaged on the surface of a mammography phantom.

The most important factor regarding the detail recorded in a radiographic image is the disparity in light and dark or shadow intensity between adjacent objects. This is called image contrast and refers to the difference in the optical density between areas or objects imaged on a detector, commonly photographic film. As xrays pass through a patient, or other objects, they are absorbed, to varying degree, by the materials through which they pass. The principal determinant of contrast is the radiation attenuation property of each material, which is a function of the material's elemental and chemical composition. Materials of higher atomic number and density (weight per volume) have a greater ability to absorb xrays and reduce or attenuate the beam.

In the diagnostic xray spectrum, for example, bone, rich in calcium, contrasts very well with the surrounding muscle and other soft tissues which have a density equivalent to water. Fatty tissue, which is only 10% less dense than muscle, is not clearly distinguished from other soft tissues because of the lack of a significant attenuation differential.

These same conditions hold for all chemical compounds and mixtures, biological and non-biological.

Image contrast, as recorded radiographically, may be expressed mathematically, for a given spectrum of xrays, as follows:

$$C = D2 - D1/D1$$

Where C=the optical contrast differential between objects D1 and D2 as recorded on a radiograph.

Where D2=the attenuating ability of object D2.

Where D1=the attenuating ability of an adjacent object or the background attenuation.

It a thin, uniform, moderate attenuator is placed in the xray bear, the overall quantity of xray in its path is uniformly and moderately reduced. Applied to the contrast equation shown above, this additional uniform attenuation shows up as an equal quantity in the numerator and the denominator. Mathematically, then, these additional figures cancel out and, C, representing the contrast differential between D2 and D1 is unchanged.

Utilizing these principles, the present invention provides a partially radiolucent, partially radiopaque marker having a uniform density and thickness for use in radiographic examination. Depending on the density of the particular tissue structure being examined and the corresponding radiation energy required, the density and thickness of the marker are selected so that upon exposure of the marker and an underlying tissue structure to the radiation, the marker will cast a legible shadow on radiographic film without obscuring radiographic anatomical detail present in the underlying tissue structure.

With regard to the range of tissue densities presented in human diagnostic radiology and the corresponding radiation energies required, those skilled in the art are well aware that soft tissue, such as breast tissue and other tissues having a density approximately that of water, require the application of "soft" radiation, generally in the range of from about 20 KV to about 40 KV. More dense tissue, such as bone tissue in the extremities, requires radiation in the range of from about 40 KV to about 70 KV. Finally, very dense tissue such as, for example, the skull, spine and the tissue structures comprising the chest, require more intense radiation in the range of from about 70 KV to about 120 KV.

Accordingly, the present invention encompasses markers of varying density and thickness which may be used for the radiographic examination of tissues representing the broad range of tissue densities noted above. In general, a marker is designed to absorb from about 2% to about 75% of the incident radiation. However, it must be appreciated that the invention is in no way limited in this regard and that the markers may absorb more or less radiation depending on the particular tissue being imaged and its density. The governing parameters are that the marker must exhibit sufficient radiolucency to provide a discernible image when exposed to radiation and at the same time exhibit sufficient radiopacity so as not to obscure the underlying tissue detail.

Thus, it is no longer necessary, as with prior art radiographic markers and methods of examination, to completely attenuate the xray beam to achieve a consistent and easily discernible image of the marker on the film. As explained more fully below in connection with the Figures, there is a broad range of materials of intermediate density which can be used to construct the markers taught by the invention.

Referring now to FIG. 1, a number of rubber O-shaped collars 10, 10 having a thickness of from about 1.5 mm to about 2 mm are shown radiographed on the surface of a Kodak mammography phantom 12. The exposure is at 28 KV, and the collars are equivalent to about 1.2 mm of aluminum, as established by the aluminum step wedge 14, which is graduated in 0.2 mm increments. Markers of this type are useful in imaging soft tissue at a radiation energy ranging from about 20 KV to about 40 KV and are particularly useful in mammography. As FIG. 1 illustrates, the markers 10 have sufficient radiopacity to cast a discernible image and are sufficiently radiolucent to permit the simulated micro calcifications 16 and fine tissue details 18 to be clearly imaged.

Figure 2:
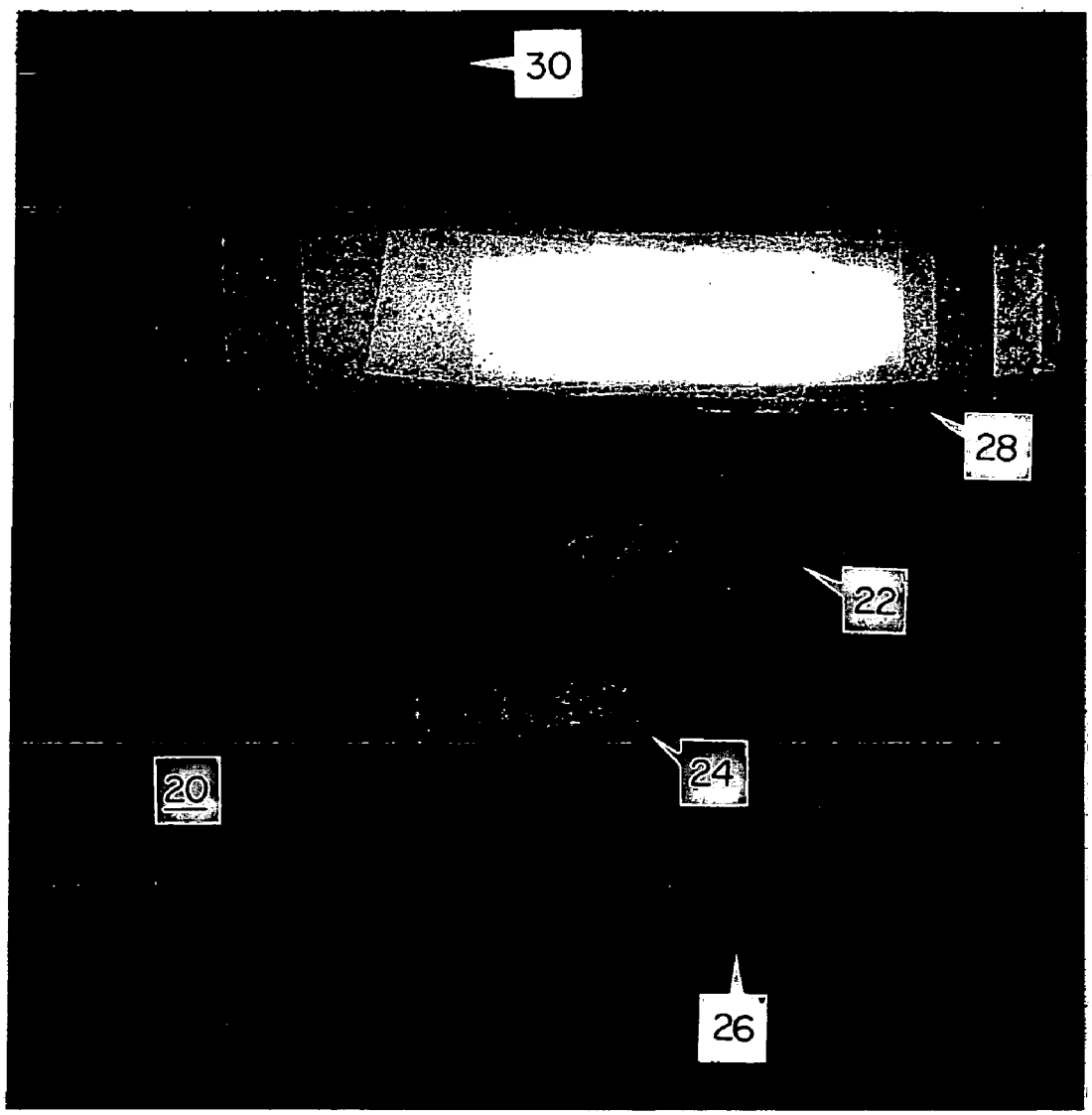
FIG. 2 is a radiograph of rubber, aluminum and vinyl markers useful in practicing the method of the present invention imaged on the surface of the American College of Radiology quality assurance phantom.

FIG. 2 illustrates additional examples of markers useful in radiographing low density tissue structures. The markers are constructed of rubber, aluminum and vinyl and are shown radiographed on the surface of the American College of Radiology quality assurance phantom ("ACR phantom 006 294"). The exposure is at 26 KV, and the radiograph was made using a photo-timed mammography machine available from General Electric. As is well-known to those skilled in the art, the ACR phantom 20 approximates breast tissue density and has simulated calcifications and nylon low density "nodules".

Markers 22, 22 comprise strips of rubber having a thickness of about 0.2 inches and a density approximately equal to 0.115 inches of aluminum. Markers 24, 24 also comprise strips of rubber, and the strips have a thickness of 0.1 inches. Markers 26, 26 comprise plastic strips having a thickness of about 0.1 inches, and markers 28, 28 are strips of aluminum having a thickness of 0.115 inches. Finally, markers 30, 30 are strips of vinyl 0.1 inches thick.

As FIG. 2 illustrates, markers comprised of these various materials cast a legible shadow without obscuring underlying detail when exposed to radiation energies typically employed in radiographing low density soft tissue. Generally, rubber markers having a thickness of from about 0.2 inches to about 0.4 inches are appropriate for radiographing soft tissue. With respect to plastic and aluminum markers, thicknesses ranging from about 0.1 inches to about 0.2 inches and from about 0.011 inches to about 0.022 inches, respectively, have been found useful. Vinyl markers provided in thicknesses ranging from about 0.75 mm to about 1 mm have been found useful.

Figure 3:
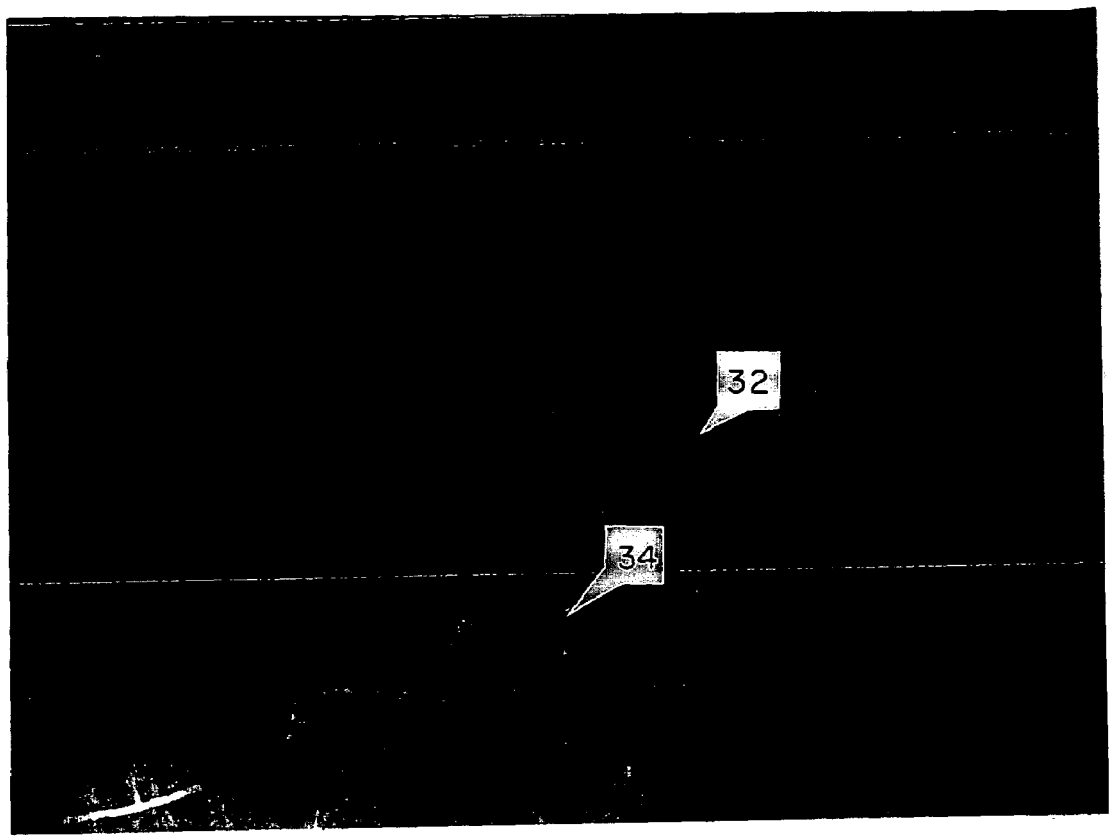
FIG. 3 is a cranio-caudal view of a patient's left breast with a vinyl marker useful in practicing the method of the invention positioned on the surface thereof.

The utility of markers constructed from vinyl for radiographing soft tissue structures without obscuring underlying detail is further illustrated in FIG. 3. FIG. 3 is a craniocaudal view of a patient's left breast 32 with a vinyl marker 34 positioned on the surface thereof to mark the location of scar tissue. As FIG. 3 illustrates, the anatomical detail in the breast tissue directly underlying the anterior marker 34 is clearly visible on the radiograph.

Figure 4:
FIG. 4(a) is a posterior view of a plastic/barium sulfate marker useful in practicing the method of the present invention radiographed on the surface of a patient's foot.
FIG. 4(b) is an oblique view of the marker shown in FIG. 4(a).

FIG. 4 illustrates posterior and oblique views of a plastic/barium sulfate marker useful for radiographing more dense tissues at energy levels from about 40 to about 70 KV. The marker 36 is plastic impregnated with 40% barium, and it is shown imaged on the surface of a patient's foot 38. Note that the anatomical detail in the bone 40 underlying the marker 36 is clearly visible.

Markers constructed of barium impregnated plastic have been found to be particularly useful in practicing the present invention because the density of the markers can be easily and precisely selected by varying the barium content of the plastic. Thus, an entire selection or system of barium impregnated plastic markers is provided for the entire range of tissue densities and exposure energies typically encountered by those skilled in the art.

Figure 5:
FIG. 5 is a radiograph of a plastic/barium sulfate marker useful in practicing the method of the present invention imaged on the surface of a patient's skull.

FIG. 5 shows a plastic/barium sulfate marker useful for radiographing very dense tissues, such as the bones of the skull, face and hip, at energy levels from about 70 to about 120 KV. The marker 42 is plastic impregnated with 40% barium and is cut from sheets measuring between 0.015–0.02 inches in thickness. The marker 42 is shown imaged on the surface of a patient's skull 44, and the radiograph shows that the marker images well at one to two layers of the sheet material (0.015–0.040 inches). The marker is most useful at a thickness of about 0.030–0.040 inches where it has sufficient density to be clearly visible on the radiograph, and yet permit sufficient penetration of the radiation to provide imaging of the diagnostic object contrast.

Figure 6:
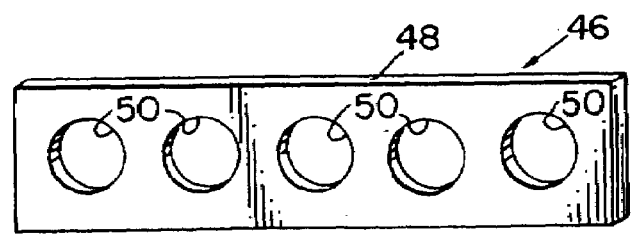
FIG. 6 is a perspective view of a marker useful for practicing the method of the invention.
Figure 7:
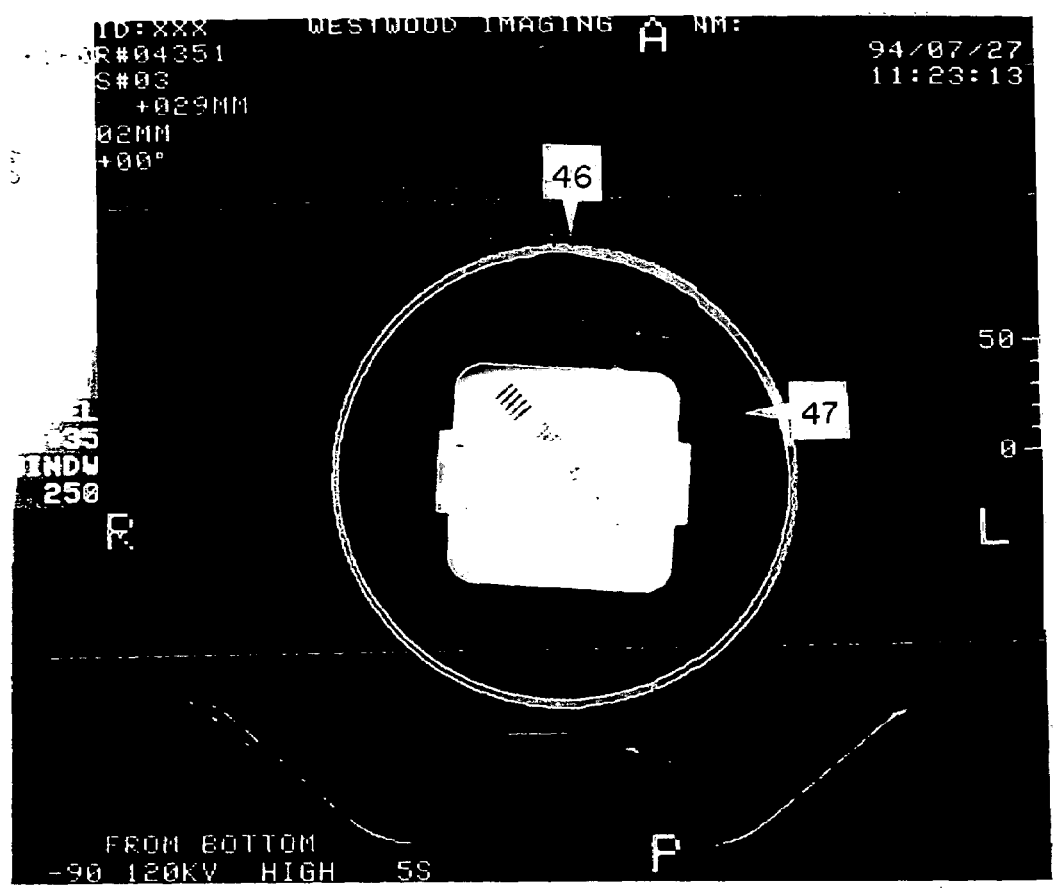
FIG. 7 is a radiograph of the marker illustrated in FIG. 6 imaged on the surface of a CT phantom.

FIG. 6 illustrates an intermediate density marker 46 useful in CT scanning applications. The marker 46 is shown imaged on the surface of a CT phantom 47 in FIG. 7. The CT phantom 47 is available from the General Electric Corporation under the designation GE #46-241-85-2GI. The marker comprises a vinyl strip 48 having a plurality of apertures 50 formed therein. When the marker is imaged together with an associated tissue structure, the apertures indicate, as illustrated in FIG. 7, whether the marker is in the axial plane and also indicates whether the CT cut is high, through the middle or low with an accuracy of plus or minus about 1 mm. In addition, the apertures provide a site for needle insertion.

The strip 48 is preferably from about 1 mm to about 4 mm in thickness; from about 1 cm to about 4 cm in width and from about 5 cm to about 20 cm in length. In the illustrated embodiment, the strip 48 is about 2 mm thick, about 2 cm wide and about 8 cm long. The apertures 50, 50 are about 1 cm in diameter and are space about 0.5 cm apart. As those skilled in the art will appreciate, the length, width and thickness of the strip may be varied as long as it is large enough to image clearly.

Markers constructed from a number of different materials and suitable for radiographing tissues representing a broad range of densities have been illustrated above. Those skilled in the art will recognize, however, that there are a great number of other marker configurations as well as other materials, either alone or in combination, which are of an intermediate density and which could just as easily be used to practice the present invention.

As noted above, the density and thickness of the marker is selected based on the density of the tissue being examined and the energy of the radiation being applied. In general markers are designed to absorb from about 2% to about 75% of the incident radiation. For example, in certain CT applications, the marker is constructed to absorb as little as from about 2% to about 5% of the incident radiation. Again, the governing parameters are that the marker must absorb enough radiation to cast a legible shadow without obscuring underlying anatomical detail.

Additional factors that influence the ultimate choice of the material from which the marker is constructed include the cost of the material, its toxicity and the ease with which the marker can be manufactured. It must also be emphasized again that the selected material must be of a uniform density so that the radiographic image of the marker has a uniform, translucent appearance without visible irregularities, conflicting striations or granulations which might obscure the resolution of anatomical detail.

The present invention further contemplates a system of partially radiolucent, partially radiopaque markers which are provided in a range of densities and thickness so that selected markers comprising the system may be used in radiographing tissue structures representing the various tissue densities enumerated above at the corresponding radiation energy range. In addition, the markers are provided in a variety of shapes to enhance the information communicated by the markers. In this regard, the markers may be shaped in accordance with a universal language, wherein each marker conveys a specific, universally accepted message. Such an enhancement of the information visibly communicated by the markers will expedite film interpretation and improve accuracy. For example, markers provided in the shape of an arrow, a triangle, the universal symbol of danger, or a standard medical cross could be provided to indicate an area of clinical concern on the film.

While preferred embodiments have been shown and described, various modifications and substitutions may be made without departing from the spirit and scope of the invention. Accordingly, it is to be understood that the present invention has been described by way of example and not by limitation.

I claim:

1. A method of radiographic examination of tissue having anatomical detail present in the tissue, comprising the steps of:
providing a source of x-ray radiation capable of generating radiation suitable for imaging the tissue;
selecting a partially radiolucent, partially radiopaque marker having a radiographic density and thickness which permit the marker to both project a radiographic shadow and transmit sufficient radiation to image anatomical detail present in the tissue when the marker and the tissue are exposed to the x-ray radiation during radiographic examination, wherein the marker comprises at least one of aluminum, rubber, plastic and vinyl, the thickness of the marker is less than about 0.4 inches, and the thickness of the marker is selected based upon the density of the tissue being examined and the energy of the radiation being applied to absorb from about 2% to about 75% of the incident radiation;
positioning the marker between the source of x-ray radiation and the tissue; and
exposing the marker and the tissue to the x-ray radiation, and generating a radiographic image of the tissue having the shadow of the marker superimposed thereon with the anatomical detail present in the tissue clearly visible through the radiographic shadow projected by the marker.

2. A method of radiographic examination as defined in claim 1, wherein the marker comprises aluminum having a thickness less than about 0.022 inches.

3. A method of radiographic examination as defined in claim 2, wherein the marker comprises aluminum having a thickness of about 0.011 to about 0.022 inches.

4. A method of radiographic examination as defined in claim 1, wherein the marker comprises rubber having a thickness less than about 0.4 inches.

5. A method of radiographic examination as defined in claim 4, wherein the marker comprises rubber having a thickness of about 0.2 to about 0.4 inches.

6. A method of radiographic examination as defined in claim 1, wherein the marker comprises plastic having a thickness less than about 0.2 inches.

7. A method of radiographic examination as defined in claim 6, wherein the marker comprises plastic having a thickness of about 0.1 to about 0.2 inches.

8. A method of radiographic examination as defined in claim 1, wherein the marker comprises plastic and metal and defines a thickness less than about 0.040 inches.

9. A method of radiographic examination as defined in claim 8, wherein the marker comprises plastic and metal and defines a thickness of about 0.015 to about 0.040 inches.

10. A method of radiographic examination as defined in claim 8, wherein the marker comprises plastic impregnated with metal.

11. A method of radiographic examination as defined in claim 1, wherein the marker comprises vinyl having a thickness less than about 1 mm.

12. A method of radiographic examination as defined in claim 11, wherein the marker comprises vinyl having a thickness of about 0.75 mm to about 1 mm.

13. A method of radiographic examination as defined in claim 1, wherein the radiographic examination is a mammographic examination and the tissue examined is breast tissue.

14. A method of mammographic examination as defined in claim 13, wherein the energy of the source of radiation is selected to be within the range of about 20 kV to about 40 kV.

15. A method of mammographic examination as defined in claim 13, wherein the marker is positioned on the patient's breast.

16. A method of radiographic examination as defined in claim 1, wherein the tissue defines a density approximately equal to at least one of a skull, spine and chest, and the energy of the source of radiation is selected to be within the range of about 70 kV to about 120 kV.

17. A method of radiographic examination of tissue having anatomical detail present in the tissue, comprising the steps of:
providing a source of x-ray radiation having a predetermined energy level capable of generating radiation suitable for imaging a predetermined tissue density;
providing a partially radiolucent, partially radiopaque marker having a radiographic density and thickness which permit the marker to both project a radiographic shadow and transmit sufficient radiation to image anatomical detail present in tissue having the predetermined tissue density, when the marker and the tissue are exposed to the predetermined level of x-ray radiation during radiographic examination, said providing step including selecting the density and thickness of the marker based on the predetermined tissue density and the predetermined energy level of the radiation provided to absorb from about 2% to about 75% of the incident radiation;
positioning the marker between the source of x-ray radiation and the tissue having the predetermined tissue density; and
exposing the marker and the tissue to the x-ray radiation at the predetermined energy level, and generating a radiographic image of the tissue having the shadow of the marker superimposed thereon with the anatomical detail present in the tissue clearly visible through the radiographic shadow projected by the marker.

18. A method of radiographic examination as defined in claim 17, wherein the marker is constructed of at least one of aluminum, rubber, plastic and vinyl, and the thickness of the marker is less than about 0.4 inches.

19. A method of radiographic examination as defined in claim 17, wherein the radiographic examination is a mammographic examination, the tissue is breast tissue having a density approximately equal to that of water, the predetermined energy level of the source of x-ray radiation is within the range of about 20 kV to about 40 kV, and the marker is positioned on a patient's breast.

20. A method of radiographic examination as defined in claim 17, wherein the marker is selected from the group including: (i) a marker comprising rubber having a thickness of less than about 0.4 inches; (ii) a marker comprising plastic having a thickness of less than about 0.2 inches; (iii) a marker comprising vinyl having a thickness of less than about 1 mm; and (iv) a marker comprising aluminum having a thickness of less than about 0.022 inches.

21. A method of radiographic examination as defined in claim 20, wherein the predetermined tissue density is approximately equal to that of water, and the predetermined energy level of the source of x-ray radiation is within the range of about 20 kV to about 40 kV.

22. A method of radiographic examination as defined in claim 17, further comprising the step of providing a plurality of different markers, each of the different markers defining a respective radiographic density and thickness different than the other markers, and corresponding to a respective tissue density.

23. A method of radiographic examination as defined in claim 22, wherein a first marker defines a first radiographic density approximately equal to the density of water; a second marker defines a second radiographic density approximately equal to the density of the bones of a patient's extremities; and a third marker defines a third radiographic density approximately equal to the density of at least one of a skull, spine or chest of a patient.

24. A method of radiographic examination as defined in claim 23, further comprising the steps of:
   (a) positioning the first marker between the source of x-radiation and tissue having a density approximately equal to the density of water, transmitting radiation within the range of about 20 kV to about 40 kV through the first marker and the tissue, and generating a radiographic image of the tissue having the shadow of the first marker superimposed thereon with the anatomical detail present in the tissue clearly visible through the radiographic shadow projected by the first marker;
   (b) positioning the second marker between the source of x-radiation and tissue having a density approximately equal to the density of the bones of a patient's extremities, transmitting radiation within the range of about 40 kV to about 70 kV through the second marker and the tissue, and generating a radiographic image of the tissue having the shadow of the second marker superimposed thereon with the anatomical detail present in the tissue clearly visible through the radiographic shadow projected by the second marker; and
   (c) positioning the third marker between the source of x-radiation and tissue having a density approximately equal to the density of at least one of a skull, spine and chest of a patient, transmitting radiation within the range of about 70 kV to about 120 kV through the third marker and the tissue, and generating a radiographic image of the tissue having the shadow of the third marker superimposed thereon with the anatomical detail present in the tissue clearly visible through the radiographic shadow projected by the third marker.

25. A method of radiographic examination as defined in claim 17, further comprising the steps of providing markers having a uniform density throughout each marker, and generating radiographic images of said markers having uniform, translucent appearances without visible irregularities, conflicting striations or granulation obscuring the resolution of the anatomical detail present in the tissue.

26. A method of radiographic examination as defined in claim 17, further comprising the steps of providing a plurality of said markers in predetermined shapes enhancing the information communicated by the markers, including:
   (a) a first marker defining the shape of a circle;
   (b) a second marker defining the shape of a triangle; and
   (c) a third marker defining the shape of a straight line.

27. A method of radiographic examination as defined in claim 26, wherein said step of providing a plurality of said markers in predetermined shapes further includes providing:
   (d) a fourth marker defining the shape of cross; and
   (e) a fifth marker in the shape of an arrow.

28. A marker for radiographic examination of tissue having anatomical detail present in the tissue, wherein a source of x-ray radiation is provided for generating radiation at a predetermined energy level suitable for imaging tissue having a predetermined tissue density, the marker is positioned between the source of x-ray radiation and the tissue, and the marker and tissue type are exposed to the x-ray radiation at the predetermined energy level to generate a radiographic image of the tissue having the shadow of the marker superimposed thereon, the marker comprising:
   a first outer surface for contacting a patient's skin; a second outer surface located on an opposite side of the marker relative to the first outer surface; and at least one partially radiolucent, partially radiopaque material located therebetween, said at least one partially radiolucent, partially radiopaque material defining a density and thickness based on the predetermined tissue density and the predetermined energy level of the radiation provided which absorbs from about 2% to about 75% of the incident radiation and, in turn, generates a radiographic image of the tissue having the shadow of the marker superimposed thereon with the anatomical detail present in the tissue clearly visible through the radiographic shadow projected by the marker.

29. A radiographic marker as defined in claim 28, wherein the partially radiopaque, partially radiolucent material is selected from the group including: (i) rubber having a thickness of less than about 0.4 inches; (ii) plastic having a thickness of less than about 0.2 inches; (iii) vinyl having a thickness of less than about 1 mm; and (iv) aluminum having a thickness of less than about 0.022 inches.

30. A radiographic marker as defined in claim 28, wherein the partially radiopaque, partially radiolucent material is selected from the group including: (i) rubber having a thickness within the range of 0.2 to about 0.4 inches; (ii) plastic having a thickness within the range of about 0.1 to about 0.2 inches; (iii) vinyl having a thickness within the range of about 0.75 mm about 1 mm; and (iv) aluminum having a thickness within the range of about 0.011 to about 0.022 inches.

31. A plurality of radiographic markers as defined in claim 28, wherein each of the plurality of markers defines a respective radiographic density and thickness different than the other markers and corresponds to a respective tissue density for imaging tissue having that density, and including (i) a first marker defining a radiographic density approximately equal to the density of water for imaging relatively soft tissue; (ii) a second marker defining a radiographic density approximately equal to the density of the bones of a patient's extremities for imaging relatively intermediate density tissue; and (iii) a third marker defining a radiographic density approximately equal to the density of at least one of a skull, spine and chest of a patient for imaging relatively dense tissue.

32. A radiographic marker as defined in claim 28, wherein the partially radiopaque, partially radiolucent material includes metal and plastic having an overall thickness of about 0.040 inches.

33. A radiographic marker as defined in claim 32, wherein the partially radiopaque, partially radiolucent material includes metal and plastic having an overall thickness of about 0.015 to about 0.040 inches.

34. A radiographic marker as defined in claim 32, wherein the plastic is impregnated with the metal.

35. A radiographic marker as defined in claim 34, wherein the plastic is impregnated with barium.

36. A marker for mammographic examination of breast tissue having anatomical detail present in the tissue, wherein a source of x-ray radiation is provided for generating radiation at a predetermined energy level suitable for imaging breast tissue, the marker is positioned between the source of x-ray radiation and the breast tissue, and the marker and breast tissue are exposed to the x-ray radiation at the predetermined energy level to generate a radiographic image of the tissue having the shadow of the marker superimposed thereon, the marker comprising:

a first outer surface for contacting a patient's breast tissue; a second outer surface located on an opposite side of the marker relative to the first outer surface; and means located between the first and second outer surfaces for generating a radiographic image of the tissue having the shadow of the marker superimposed thereon with the anatomical detail present in the tissue clearly visible through the radiographic shadow projected by the marker.

37. A mammography marker as defined in claim 36, wherein said means includes at least one partially radiolucent, partially radiopaque material defining a density and thickness based on the breast tissue density and the predetermined energy level of the radiation provided which absorbs from about 2% to about 75% of the incident radiation.

38. A mammography marker as defined in claim 37, wherein the partially radiopaque, partially radiolucent material is selected from the group including: (i) rubber having a thickness of less than about 0.4 inches; (ii) plastic having a thickness of less than about 0.2 inches; (iii) vinyl having a thickness of less than about 1 mm; and (iv) aluminum having a thickness of less than about 0.022 inches.

39. A mammography marker as defined in claim 38, wherein the plastic is impregnated with the metal.

40. A method of mammographic examination of breast tissue having anatomical detail present in the tissue, comprising the steps of:

providing a source of x-ray radiation having a predetermined energy level capable of generating radiation suitable for imaging breast tissue;

providing a partially radiolucent, partially radiopaque marker having a radiographic density and thickness which permit the marker to both project a radiographic shadow and transmit sufficient radiation to image anatomical detail present in breast tissue when the marker and the tissue are exposed to the predetermined level of x-ray radiation during mammographic examination;

positioning the marker between the source of x-ray radiation and the breast tissue; and exposing the marker and the tissue to the x-ray radiation at the predetermined energy level, and generating a radiographic image of the tissue having the shadow of the marker superimposed thereon with the anatomical detail present in the tissue clearly visible through the radiographic shadow projected by the marker.

41. A method of mammographic examination as defined in claim 40, wherein said providing step includes selecting the density and thickness of the marker based on the breast tissue density and the predetermined energy level of the radiation provided to absorb from about 2% to about 75% of the incident radiation.

42. A method of mammographic examination as defined in claim 40, further comprising the steps of adhesively securing the marker to a patient's breast tissue such that the marker is positioned between the source of x-radiation and the breast tissue, transmitting radiation within the range of about 20 kV to about 40 kV through the marker and the underlying breast tissue, and generating a radiographic image of the tissue having the shadow of the marker superimposed thereon with the anatomical detail present in the tissue clearly visible through the radiographic shadow projected by the marker.

* * * * *